United States Patent [19]

Loeffler et al.

[11] 4,414,208
[45] Nov. 8, 1983

[54] O,S-DIALKYL-O-(4-FLUOROPHENYL)-(DI)-THIOPHOSPHORIC ACID ESTERS, AND THE USE THEREOF FOR COMBATING PESTS

[75] Inventors: Hans-Peter Loeffler, Ludwigshafen; Heinrich Adolphi, Limburgerhof, both of Fed. Rep. of Germany

[73] Assignee: BASF Aktiengesellschaft, Fed. Rep. of Germany

[21] Appl. No.: 337,076

[22] Filed: Jan. 4, 1982

Related U.S. Application Data

[63] Continuation of Ser. No. 166,572, Jul. 7, 1980, abandoned.

[51] Int. Cl.³ .................. C07F 9/165; A01N 57/14
[52] U.S. Cl. .................. 424/224; 260/940; 260/948; 260/950; 260/954; 260/951; 260/949
[58] Field of Search .................. 260/964; 424/224

[56] References Cited

U.S. PATENT DOCUMENTS 3,683,053  8/1972  Kishino et al. .................. 260/950
3,763,288  10/1973  Kishino et al. .................. 260/949
4,028,438  6/1977  Tsuchiya et al. .................. 260/948

FOREIGN PATENT DOCUMENTS 482460  6/1976  U.S.S.R. .................. 260/964

Primary Examiner—Anton H. Sutto
Attorney, Agent, or Firm—Keil & Witherspoon

[57] ABSTRACT

Novel O,S-dialkyl-O-(4-fluorophenyl)-(di)thiophosphoric acid esters of the formula

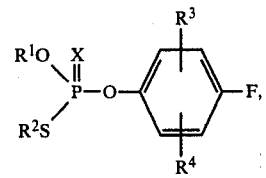

where $R^1$ is alkyl of from 1 to 3 carbon atoms, $R^2$ is alkyl of from 1 to 5 carbon atoms, cycloalkyl of 5 or 6 carbon atoms, alkoxyalkyl of from 2 to 7 carbon atoms or alkylthioalkyl of from 2 to 7 carbon atoms, $R^3$ is hydrogen, halogen, alkyl of from 1 to 4 carbon atoms, haloalkyl, alkoxy or alkylthio, each of from 1 to 4 carbon atoms, cyano or nitro, $R^4$ denotes halogen, alkyl of from 1 to 4 carbon atoms, haloalkyl, alkoxy or alkylthio, each of from 1 to 4 carbon atoms, cyano or nitro, and X is oxygen or sulfur, $R^4$ additionally denoting hydrogen when X is sulfur or when X is oxygen and $R^2$ is methyl, n-propyl, sec-butyl, isobutyl, tert-butyl or pentyl, which compounds are valuable pesticides.

3 Claims, No Drawings

O,S-DIALKYL-O-(4-FLUOROPHENYL)-(DI)THIO-PHOSPHORIC ACID ESTERS, AND THE USE THEREOF FOR COMBATING PESTS

This is a continuation of application Ser. No. 166,572, filed July 7, 1980, now abandoned.

The present invention relates to O,S-dialkyl-O-(fluorophenyl)-(di)thiophosphoric acid esters, their manufacture, their use for combating pests, and agents therefor.

Insecticidally effective O,O-dialkyl-O-(4-fluorophenyl)-thionophosphoric acid esters have been disclosed (Agrochemia, Bratislava, 5, 24–28, 1965, Pestic. Sci., 4, 701–705, 1973, Soviet Union Pat. No. 482,460 and German Printed Application DE-AS No. 2,163,391).

We have now found that O,S-dialkyl-O-(4-fluorophenyl)-(di)thiophosphoric acid esters of the formula

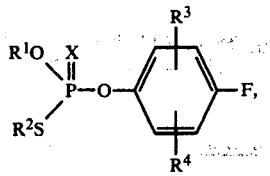

where $R^1$ is alkyl of from 1 to 3 carbon atoms, $R^2$ is alkyl of from 1 to 5 carbon atoms, cycloalkyl of 5 or 6 carbon atoms, alkoxyalkyl of from 2 to 7 carbon atoms or alkylthioalkyl of from 2 to 7 carbon atoms, $R^3$ is hydrogen, halogen, alkyl of from 1 to 4 carbon atoms, haloalkyl, alkoxy or alkylthio, each of from 1 to 4 carbon atoms, cyano or nitro, $R^4$ denotes halogen, alkyl of from 1 to 4 carbon atoms, haloalkyl, alkoxy or alkylthio, each of from 1 to 4 carbon atoms, cyano or nitro, and X is oxygen or sulfur, $R^4$ additionally denoting hydrogen when X is sulfur or when X is oxygen and $R^2$ is methyl, n-propyl, sec-butyl, isobutyl, tert-butyl or pentyl, effectively combat pests from the classes of insects and Arachnida. Their action is superior to that of the prior art O,O-dialkyl-O-(4-fluorophenyl)-(di)thionophosphoric acid esters.

In formula I, $R^1$ denotes alkyl of from 1 to 3 carbon atoms, such as methyl, ethyl, n-propyl and isopropyl, $R^2$ denotes alkyl of from 1 to 5 carbon atoms, such as methyl, ethyl, propyl, butyl and pentyl; cycloalkyl of 5 or 6 carbon atoms, such as cyclopentyl and cyclohexyl; alkoxyalkyl of from 2 to 7, especially 2 to 4, carbon atoms, such as 2-methoxyethyl and 2-ethoxyethyl; or alkylthioalkyl of from 2 to 7, especially 2 to 4, carbon atoms, such as 2-methylthioethyl and 2-ethylthioethyl, X denotes oxygen or sulfur, and $R^3$ and $R^4$ denote hydrogen; halogen, such as fluorine, chlorine and bromine; alkyl of from 1 to 4 carbon atoms, such as methyl and ethyl; haloalkyl, alkoxy or alkylthio, each of from 1 to 4 carbon atoms, such as trifluoromethyl, methylthio or methoxy; cyano; or nitro. $R^4$ only denotes hydrogen when X is sulfur, or when X is oxygen and $R^2$ is methyl, n-propyl, sec-butyl, isobutyl, tert-butyl or phenyl.

The present invention further relates to a process for the manufacture of O,S-dialkyl-(4-fluorophenyl)-(di)thiophosphoric acid esters of the formula 1, wherein an O,S-dialkylphosphoric acid ester chloride of the formula

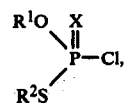

where $R^1$, $R^2$ and X have the meanings given in claim 1, is reacted with a phenol of the formula

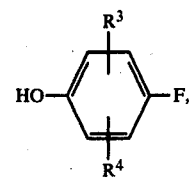

where $R_3$ and $R^4$ have the meanings given in claim 1, in the presence of a solvent or diluent and in the presence or absence of an acid binder.

The reaction is carried out in organic solvents or diluents, such as acetonitrile, toluene or methyl ethyl ketone, or in 2-phase systems, such as toluene/water or dichloromethane/water. Advantageously, from 1 to 2 moles of acid binder are used per mole of phenol of the formula III. Suitable examples are bases, such as alkali metal carbonates, e.g., potassium carbonate, alkali metal hydroxides, e.g., sodium hydroxide, and tertiary amines, e.g., triethylamine. Instead of base and phenol, a salt of a phenol may also be used. The reaction is carried out at from room temperature to 100° C.

The starting materials are employed in equimolar amounts. It may in some cases be advantageous to use an excess of the one or the other reaction component.

The phenols of the formula III used as starting materials may be manufactured from the corresponding fluorinated anilines (German Laid-Open Application DE-OS No. 2,426,994).

2-Halo-4-fluorophenols may be synthesized from 4-fluorophenol by halogenation (Zh. Obshch. Khim., 37, 2486, 1967). The phosphoric acid ester chlorides of the formula II may also be manufactured by processes disclosed in the literature (German Printed Application DE-AS No. 2,642,982; J. Org. Chem., 30, 3217, 1965).

The compounds of the formula I according to the invention may also be obtained from phosphorous acid esters of the formula IV in an Arbusov reaction by reaction with sulfenyl chlorides, in accordance with the following equation:

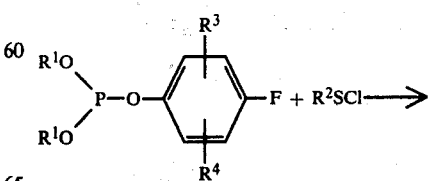

-continued

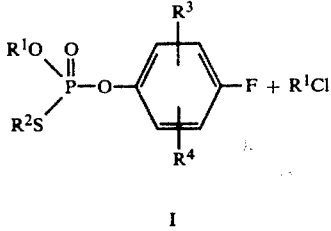

I

The compounds are also accessible by alkylation of salts of the formula V with an alkylating agent $R^2Y$:

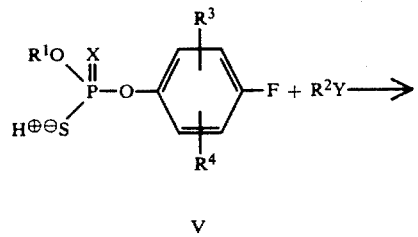

V

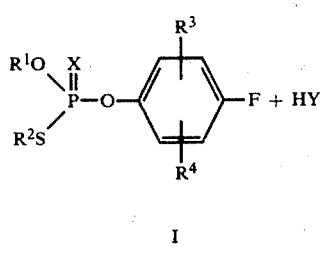

I

Suitable alkylating agents are, for example, halides of the formula $R^2Y$, Y denoting halogen and $R^2$ having the above meanings, such as 2-bromobutane and 1-chloropropane.

It is also possible to obtain the compounds by reaction of O-(4-fluorophenyl)-phosphoric acid ester dichlorides of the formula VI with alcohols and mercaptans:

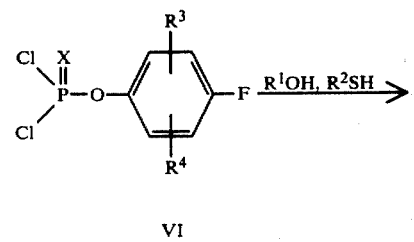

VI

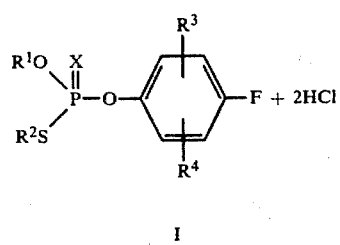

I

In the above equations, the substituents $R^1$, $R^2$, $R^3$, $R^4$ and X have the meanings given above.

The following example illustrates the manufacture of the compounds according to the invention.

EXAMPLE

At $-20°$ C., 15.3 ml of bromine is dripped into 33.6 g of 4-fluorophenol in 300 ml of dichloromethane. After the solution has stood for 24 hours it is colorless. Distillation gives 46 g of 2-bromo-4-fluorophenol of boiling point 70° C./13.3 mbars.

9.7 g of potassium carbonate is added to 13.4 g of bromo-4-fluorophenol dissolved in 100 ml of acetonitrile and the mixture is heated for 1 hour at 50° C. while stirring. 13.2 g of O-ethyl-S-n-propylthiophosphoric acid ester chloride is then dripped in and the resultant mixture stirred for 12 hours at room temperature. The solvent is removed in a rotary evaporator, 400 ml of toluene and 100 ml of water are added, the phases are separated, and the organic phase is washed with 2 N sodium hydroxide solution and then with water, and dried with sodium sulfate, and the solvent and volatile impurities are removed under reduced pressure at 40° C./0.13 mbar. The residue is 18.5 g of O-ethyl-S-n-propyl-O-(2-bromo-4-fluorophenyl)-thiophosphate; $n_D^{26}$: 1.5235.

The following compounds may be obtained for example analogously or by one of the processes described above:

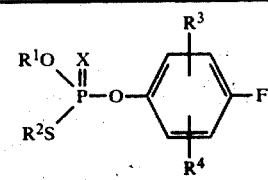

| No. | $R^1$ | $R^2$ | X | $R^3$ | $R^4$ | $n_D$ |
|---|---|---|---|---|---|---|
| 1 | CH₃ | n-C₃H₇ | S | H | H | |
| 2 | C₂H₅ | n-C₃H₇ | O | H | 2-Br | $n_D^{26}$1.5235 |
| 3 | CH₃ | n-C₃H₇ | O | H | H | |
| 4 | " | sec-C₄H₉ | O | H | H | |
| 5 | " | sec-C₄H₉ | S | H | H | |
| 6 | " | n-C₃H₇ | O | H | 2-Br | |
| 7 | " | sec-C₄H₉ | O | H | 2-Cl | |
| 8 | " | n-C₃H₇ | O | H | 3-Cl | |
| 9 | C₂H₅ | n-C₃H₇ | O | H | H | $n_D^{24}$1.4973 |
| 10 | " | " | O | H | 2-Cl | $n_D^{24}$1.5110 |
| 11 | " | " | O | H | 2-F | $n_D^{25}$1.5145 |
| 12 | " | " | O | H | 3-Cl | |
| 13 | " | " | O | H | 3-F | |
| 14 | " | " | O | H | 3-CH₃ | |
| 15 | " | " | O | 6-Cl | 2-Cl | |
| 16 | " | " | O | H | 2-CN | |
| 17 | " | " | O | H | 2-SCH₃ | |
| 18 | " | " | S | H | H | $n_D^{26}$1.5360 |
| 19 | " | " | S | H | 2-Cl | $n_D^{21}$1.5470 |
| 20 | " | " | S | H | 2-Br | $n_D^{24}$1.5602 |
| 21 | " | " | S | H | 2-F | |
| 22 | " | " | S | H | 3-Cl | $n_D^{25}$1.5463 |
| 23 | " | " | S | H | 3-F | |
| 24 | " | " | S | H | 3-CH₃ | |
| 25 | " | " | S | 6-Cl | 2-Cl | oil |
| 26 | " | " | S | H | 2-CH₃ | |
| 27 | " | " | S | H | 2-CN | |
| 28 | " | " | S | H | 2-SCH₃ | |
| 29 | " | i-C₃H₇ | O | H | 2-Cl | |
| 30 | " | " | O | H | 2-Br | |
| 31 | " | " | O | H | 2-CH₃ | |
| 32 | " | " | O | H | 3-Cl | |
| 33 | " | " | O | H | 3-F | |
| 34 | " | " | S | H | 2-Cl | |
| 35 | " | " | S | H | 2-Br | |
| 36 | " | " | S | H | 2-CH₃ | |
| 37 | " | " | S | H | 3-Cl | |
| 38 | " | " | S | H | 3-F | |
| 39 | " | sec-C₄H₉ | O | H | H | $n_D^{25}$1.5004 |
| 40 | " | " | O | H | 2-Cl | $n_D^{21}$1.5120 |

-continued

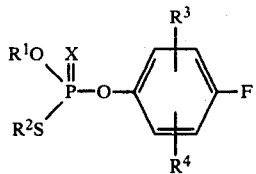

| No. | R¹ | R² | X | R³ | R⁴ | $n_D$ |
|---|---|---|---|---|---|---|
| 41 | " | " | O | H | 2-Br | $n_D^{29}1.5206$ |
| 42 | " | " | O | H | 2-F | |
| 43 | " | " | O | H | 3-F | |
| 44 | " | " | O | H | 3-Cl | $n_D^{22}1.515$ |
| 45 | " | " | O | H | 3-F | |
| 46 | " | " | O | 6-Cl | 2-Cl | |
| 47 | " | " | O | 6-Br | 2-Br | |
| 48 | " | " | O | 6-Br | 2-Br | |
| 49 | " | " | O | H | 3-CH₃ | |
| 50 | " | " | O | H | 2-CH₃ | |
| 51 | " | " | S | H | H | $n_D^{25}1.5320$ |
| 52 | " | " | S | H | 2-Cl | $n_D^{22}1.5421$ |
| 53 | " | " | S | H | 2-Br | $n_D^{30}1.5530$ |
| 54 | " | " | S | H | 2-F | |
| 55 | " | " | S | H | 3-Cl | $n_D^{22}1.5466$ |
| 56 | " | " | S | H | 3-F | |
| 57 | " | " | S | 6-Cl | 2-Cl | |
| 58 | " | " | S | 6-Br | 2-Br | |
| 59 | " | " | S | H | 3-CH₃ | |
| 60 | " | " | S | H | 2-CH₃ | |
| 61 | " | i-C₄H₉ | O | H | H | |
| 62 | " | " | O | H | 3-Cl | |
| 63 | " | " | O | H | 2-Cl | |
| 64 | " | " | O | H | 2-Br | |
| 65 | " | " | S | H | H | $n_D^{28}1.5282$ |
| 66 | " | " | S | H | 3-Cl | $n_D^{22}1.5400$ |
| 67 | " | " | S | H | 2-Cl | $n_D^{26}1.5375$ |
| 68 | " | " | S | H | 2-Br | |
| 69 | " | CH₃O—(CH₂)₂— | O | H | H | |
| 70 | " | " | O | H | 2-Cl | $n_D^{23}1.5146$ |
| 71 | " | " | O | H | 2-Br | $n_D^{32}1.5220$ |
| 72 | " | " | O | H | 3-Cl | $n_D^{24}1.5159$ |
| 73 | " | CH₃—S—(CH₂)₂— | O | H | H | |
| 74 | " | " | O | H | 2-Cl | |
| 75 | " | " | O | H | 2-Br | |
| 76 | " | " | O | 2-Cl | 6-Cl | |
| 77 | " | " | O | 2-Br | 6-Br | |
| 78 | CH₃ | " | O | H | 2-Cl | |
| 79 | " | " | O | H | 2-Br | |
| 80 | C₂H₅ | C₂H₅—S—(CH₂)₂— | O | H | 2-Cl | |
| 81 | " | " | O | H | 2-Br | |
| 82 | " | " | O | 2-Cl | 6-Cl | |
| 83 | " | " | O | 6-Br | 2-Br | |
| 84 | " | C₅H₁₁ | O | H | H | |
| 85 | " | " | O | H | 2-Br | |
| 86 | " | " | O | H | 2-Cl | |
| 87 | " | " | S | H | H | |
| 88 | " | " | S | H | 2-Cl | |
| 89 | " | " | S | H | 2-Br | |
| 90 | " | n-C₃H₇—CH(CH₃)— | O | H | H | |
| 91 | " | " | O | H | 2-Br | |

The O,S-dialkyl-(4-fluorophenyl)-(di)thiophosphoric acid esters of the formula I according to the invention are suitable for effectively combating pests from the classes of insects and Arachnida.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diasbrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Musca domestica, Mayetiola destructor, Dasyneura brassicae, Contarinia tritici, Haplodiplosis equestris, Tipula paludosa, Tipula oleracea, Dacus cucurbitae, Dacus oleae, Ceratitis captitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* an example from the Isoptera order is *Reticulitermes lucifugus.*

Examples of mites and ticks (Acarina) belonging to the Arachnica class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

The compounds according to the invention may be successfully employed as pesticides for crop protection, and in the hygiene, stores protection and veterinery sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below:

I. 3 parts by weight of O-ethyl-S-n-propyl-O-(3-chloro-4-fluorophenyl)-thiophosphate is intimately mixed with 97 parts by weight of particulate kaolin. A dust is obtained containing 3% by weight of the active ingredient.

II. 30 parts by weight of O-ethyl-S-n-propyl-O-(3-chloro-4-fluorophenyl)-thiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of O-ethyl-S-isobutyl-O-(4-fluorophenyl)-dithiophosphate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of O-ethyl-S-sec-butyl-O-(3-chloro-4-fluorophenyl)-thiophosphate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4- chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-pnenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-( 6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-metnano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(+)-cis,trans-2,2-dimethyl-3-(2,2-dichlorovinyl)-cyclopropanecarboxylate, α-cyano-3-phenoxybenzyl(+)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophtnalimidoethyl-DL-cis,trans-chrysanthemate, 2-methyl-5-(2-propynyl)-3-furylmethyl-chrysanthemate, and α-cyano-3pnenoxybenzyl-α-isopropyl-4-chlorophenylacetate.

The following examples demonstrate the biological action of the novel compounds. The prior art compound

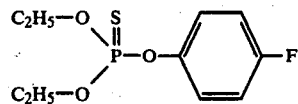

(Pestic. Sci., 4, 703, 1973) was used for comparison purposes. The other active ingredients are numbered as in the table above.

EXAMPLE A

Contact action on oriental cockroaches (*Blatta orientalis*)

The bottom of 1-liter preserving jars is treated with acetonic solutions of the active ingredients. After the solvent has evaporated, 5 adult cockroaches are introduced into each jar.

The kill rate is determined after 48 hours.

| Active ingredient | Amount of active ingredient per jar (mg) | Kill rate (%) |
|---|---|---|
| 2 | 0.04 | 80 |
| 9 | 0.1 | 100 |
| 10 | 0.04 | 100 |
| 12 | 0.1 | 100 |
| 39 | 0.04 | 100 |
| 40 | 0.1 | 100 |
| 41 | 0.1 | 100 |
| 51 | 0.1 | 100 |
| 52 | 0.04 | 100 |
| 66 | 0.1 | 100 |
| 69 | 0.04 | 80 |
| 70 | 0.1 | 100 |
| 71 | 0.1 | 100 |

EXAMPLE B

Contact action on houseflies (*Musca domestica*); continuous contact

Both covers and bottoms of Petri dishes 10 cm in diameter are lined with a total per dish of 2 ml of acetonic solutions of the active ingredients. After the solvent has evaporated (about 30 mins.), 10 flies are introduces into each dish. The kill rate is determined after 4 hours.

| Active ingredient | Amount of active ingredient per dish (mg) | Kill rate (%) |
|---|---|---|
| 9 | 0.01 | 100 |
| 10 | 0.001 | 80 |
| 19 | 0.01 | 80 |
| 20 | 0.02 | 100 |
| 39 | 0.005 | 100 |

-continued

| Active ingredient | Amount of active ingredient per dish (mg) | Kill rate (%) |
|---|---|---|
| 40 | 0.002 | 80 |
| 41 | 0.005 | 100 |
| 44 | 0.005 | 100 |
| 51 | 0.01 | 80 |
| 52 | 0.01 | 100 |
| 65 | 0.01 | 100 |
| 66 | 0.02 | 100 |
| 69 | 0.02 | 100 |

EXAMPLE C

Contact action on houseflies (*Musca domestica*)

1 μl of the active ingredient disclosed in acetone is administered by means of a micrometer syringe to the ventral abdomen of 4-day old imagoes under slight $CO_2$ narcosis. 20 animals treated in the same way are then placed in a plastic bag having a volume of approx. 500 ml.

The animals in supine position are counted after 4 days and the $LD_{50}$ is determined by means of a graph.

| Active ingredient | $LD_{50}$ (μg/fly) |
|---|---|
| 9 | 0.095 |
| 10 | 0.06 |
| 12 | 0.09 |
| 39 | 0.1 |
| 40 | 0.04 |
| 41 | 0.07 |
| 44 | 0.09 |

EXAMPLE D

Breeding experiment with houseflies (*Musca domestica*)

50 g of a culture medium consisting of 100 parts of water, 10 parts of baker's yeast, 10 parts of dried milk, and 1 part of agar is thoroughly mixed, while warm, with aqueous formulations of the active ingredients.

After the culture medium has cooled, approx. 0.1 ml of flies' eggs is placed on it and their development observed for a week.

The temperature is maintained at 20° C.

| Active ingredient | Concentration in culture medium (ppm) | |
|---|---|---|
| 2 | 1.0 | no hatching |
| 9 | 0.1 | considerable inhibition |
| 10 | 0.5 | no hatching |
| 18 | 2.5 | no hatching |
| 19 | 2.5 | no hatching |
| 20 | 2.5 | no hatching |
| 39 | 1.0 | no hatching |
| 40 | 2.5 | no hatching |
| 41 | 1.0 | no hatching |
| 44 | 2.5 | no hatching |
| 51 | 2.5 | no hatching |
| 65 | 2.5 | no hatching |
| 66 | 2.5 | no hatching |
| 71 | 2.5 | no hatching |

EXAMPLE E

Contact action and effect of ingested food on caterpillars of the diamondback moth (*Plutella maculipennis*)

Leaves of young cabbage plants are dipped for 3 seconds into aqueous emulsions of the active ingredients and placed, after excess liquid has been briefly allowed to drip off, on a moist filter paper in a Petri dish. 10 caterpillars in the 4th stage are then placed on each leaf. The action is assessed after 48 hours.

| Active ingredient | Active ingredient concentration in emulsion (%) | Kill rate (%) |
|---|---|---|
| 2 | 0.004 | 80 |
| 9 | 0.002 | 80 |
| 10 | 0.002 | 100 |
| 12 | 0.002 | 80 |
| 18 | 0.005 | 100 |
| 19 | 0.004 | 80 |
| 20 | 0.005 | 100 |
| 22 | 0.005 | 100 |
| 39 | 0.001 | 100 |
| 40 | 0.001 | 100 |
| 41 | 0.002 | 100 |
| 44 | 0.002 | 100 |
| 50 | 0.002 | 80 |
| 51 | 0.004 | 100 |
| 52 | 0.004 | 100 |
| 54 | 0.005 | 100 |
| 69 | 0.001 | 80 |
| 70 | 0.004 | 100 |
| 71 | 0.004 | 100 |
| Comparative agent I | 0.02 | <80 |

EXAMPLE F

Contact action on ticks (*Ornithodorus moubata*)

Ticks in the 3rd larval stage are placed in paper bags which are dipped for 3 seconds into emulsions of the active ingredients. The bags are then suspended. The action on the ticks is assessed after 48 hours.

| Active ingredient | Active ingredient concentration in emulsion (%) | Kill rate (%) |
|---|---|---|
| 9 | 10 | 100 |
| 39 | 20 | 100 |
| 40 | 10 | 100 |
| 44 | 50 | 100 |
| 69 | 50 | 100 |

EXAMPLE G

Action on spider mites (*Tetranychus telarius*)

Potted bush beans which have developed the first pair of true leaves and are heavily infested with all stages of the spinning mite *Tetranychus telarius* are sprayed to runoff in a spray booth with aqueous formulations of the active ingredients. The plants are placed on a rotating plate and are sprayed from all sides with 50 ml of spray liquor. Spraying lasts about 22 seconds.

The number of living spinning mites is ascertained after 8 days.

| Active ingredient | Active ingredient concentration in formulation (%) | Kill rate (%) |
|---|---|---|
| 2 | 0.005 | 100 |
| 10 | 0.01 | 100 |
| 22 | 0.02 | 100 |
| 25 | 0.02 | 100 |
| 41 | 0.01 | 100 |
| 69 | 0.02 | 100 |
| 70 | 0.008 | 100 |
| Comparative agent I | 0.1 | 80 |

We claim:

1. O,S-Dialkyl-O-(4-fluorophenyl)-(di)thiophosphoric acid esters of the formula

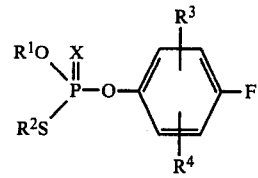

where $R^1$ is ethyl, $R^2$ is propyl or butyl, $R^3$ is hydrogen, or halogen, $R^4$ is hydrogen, halogen or methyl and X is oxygen or sulfur.

2. A pesticide comprising a solid or liquid carrier and a pesticidally effective amount of at least one O,S-dialkyl-O-(4-fluorophenyl)-(di)thiophosphoric acid ester of claim 1.

3. A process for combating insects and Arachnida pests, wherein O,S-dialkyl-O-(4-fluorophenyl-(di)thiophosphoric acid esters of claim 1 are allowed to act on the pests of their habitat.

* * * * *

UNITED STATES PATENT AND TRADEMARK OFFICE
CERTIFICATE OF CORRECTION

PATENT NO. : 4,414,208

DATED : November 8, 1983

INVENTOR(S) : Hans-Peter LOEFFLER et al.

It is certified that error appears in the above-identified patent and that said Letters Patent is hereby corrected as shown below:

On Title page of Patent please add:

-- [30]   Foreign Application Priority Data
     July 18, 1979 (DE) Federal Republic
     of Germany 2928978 --

*Signed and Sealed this*

*Third* Day of *January 1984*

[SEAL]

*Attest:*

GERALD J. MOSSINGHOFF

*Attesting Officer*   *Commissioner of Patents and Trademarks*